US008685915B2

(12) United States Patent
Hettwer et al.

(10) Patent No.: US 8,685,915 B2
(45) Date of Patent: Apr. 1, 2014

(54) MODIFIED AGRIN-FRAGMENT CAPABLE OF RESTORING MUSCLE STRENGTH FOR USE AS A MEDICAMENT

(75) Inventors: Stefan Hettwer, Zurich (CH); Stefan Kucsera, Aurau (CH); Jan Willem Vrijbloed, Mohlin (CH)

(73) Assignee: Neurotune AG, Schlieren (CH)

( * ) Notice: Subject to any disclaimer, the term of this patent is extended or adjusted under 35 U.S.C. 154(b) by 0 days.

(21) Appl. No.: 13/393,662

(22) PCT Filed: Sep. 1, 2010

(86) PCT No.: PCT/EP2010/005372
§ 371 (c)(1),
(2), (4) Date: May 1, 2012

(87) PCT Pub. No.: WO2011/026615
PCT Pub. Date: Mar. 10, 2011

(65) Prior Publication Data
US 2012/0208765 A1    Aug. 16, 2012

(30) Foreign Application Priority Data

Sep. 4, 2009    (EP) .................................... 09011367

(51) Int. Cl.
*C07K 14/00*    (2006.01)

(52) U.S. Cl.
USPC .......................................... 514/1.1; 530/350

(58) Field of Classification Search
None
See application file for complete search history.

(56) References Cited

U.S. PATENT DOCUMENTS

2008/0295186 A1    11/2008    Sonderegger et al.

FOREIGN PATENT DOCUMENTS

| WO | 97/21811 A2 | 6/1997 |
| WO | 2006/103261 A9 | 10/2006 |
| WO | 2008/074813 A2 | 6/2008 |

OTHER PUBLICATIONS

Reif et al., Specific cleavage of agrin by neurotrypsin, a synaptic protease linked to mental retardation, Nov. 1, 2007, The FASEB Journal 21(13):3468-3478.*
Bezakova Gabriela et al: "New insights into the roles of agrin"; Nature Reviews Molecular Cell Biology; MacMillan Magazines, London, Great Britain; vol. 4, No. 4; Apr. 1, 2003; pp. 295-308; XP008080787.
Gesemann M et al: "Acetylcholine receptor-aggregating activity of agrin isoforms and mapping of the active site"; The Journal of Cell Biology; Rockefeller University Press; vol. 128, No. 4, Feb. 1, 1995; pp. 625-636, XP002440442.
Matsumoto-Miyai Kazumasa et al: "Coincident Pre- and Postsynaptic Activation Induces Dendritic Filopodia via Neurotrypsin-Dependent Agrin Cleavage"; Cell; vol. 136; No. 6; Mar. 2009; pp. 1161-1171; XP002558394.
Burgess Robert W et al: "Alternatively spliced isoforms of nerve-and muscle-derived agrin: Their roles at the neuromuscular junction"; NEURON; vol. 23, No. 1; May 1999; pp. 33-44; XP002558395.
Bauer, J. M. et al.; (2008). Sarcopenia and frailty: a clinician's controversial point of view. Exp. Gerontol. 43, 674-678.
Bezakova, G. et al.; (2003). New insights into the roles of agrin. Nat. Rev. Mol. Cell Biol. 4, 295-308.
Gschwend, T. P. et al.; (1997). Neurotrypsin, a novel multidomain serine protease expressed in the nervous system. Mol. Cell Neurosci. 9, 207-219.
Lauretani, F. et al.; (2003). Age-associated changes in skeletal muscles and their effect on mobility: an operational diagnosis of sarcopenia. J Appl. Physiol 95, 1851-1860.
Molinari, F., et al.; (2002). Truncating neurotrypsin mutation in autosomal recessive nonsyndromic mental retardation. Science 298, 1779-1781.
Reif, R., et al.; (2007). Specific cleavage of agrin by neurotrypsin, a synaptic protease linked to mental retardation. FASEB J 21, 3468-3478.
Song, Y. et al.; (2008). New dogs in the dogma: Lrp4 and Tid1 in neuromuscular synapse formation. Neuron 60, 526-528.
Stephan, A. et al.; (2008). Neurotrypsin cleaves agrin locally at the synapse. FASEB J.

* cited by examiner

*Primary Examiner* — John Ulm
(74) *Attorney, Agent, or Firm* — Rankin, Hill & Clark LLP

(57) ABSTRACT

Modified agrin fragment having in vivo activity, comprising at least the domains LG2 and LG3 of human agrin in covalently interlinked form and modified in such a way that the fragment cannot be cleaved by neurotrypsin for use as medicament.

12 Claims, 6 Drawing Sheets

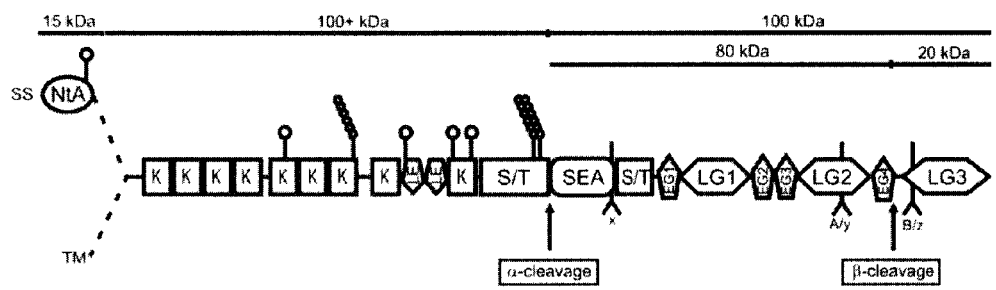

Fig 1

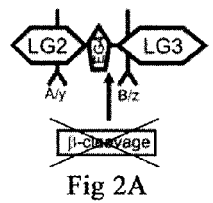

Fig 2A

```
LADFNGFSHL  ELRGLHTFAR  DLGEKMALEV  VFLARGPSGL  LLYNGQKTDG  KGDFVSLALR   60
DRRLEFRYDL  GKGAAVIRSR  EPVTLGAWTR  VSLERNGRKG  ALRVGDGPRV  LGESPKSRKV  120
PHTVLNLKEP  LYVGGAPDFS  KLARAAAVSS  GFDGAIQLVS  LGGRQLLTPE  HVLRQVDVTS  180
FAGHPCTRAS  GHPCLNGASC  VPREAAYVCL  CPGGFSGPHC  EKGLVEASAG  DVDTLAFDGR  240
TFVEYLNAVT  ESELANEIPV  EKALQSNHFE  LSLRTEATQG  LVLWSGKATE  RADYVALAIV  300
DGHLQLSYNL  GSQPVVLRST  VPVNTNRWLR  VVAHREQREG  SLQVGNEAPV  TGSSPLGATQ  360
LDTDGALWLG  GLPELPVGPA  LPKAYGTGFV  GCLRDVVVGR  HPLHLLEDAV  TKPELRPCPT  420
P                                                                      421
```

Fig 2B

```
LADFNGFSHL ELRGLHTFAR DLGEKMALEV VFLARGPSGL LLYNGQKTDG KGDFVSLALR   60
DRRLEFRYDL GKGAAVIRSR EPVTLGAWTR VSLERNGRKG ALRVGDGPRV LGESPVPHTV  120
LNLKEPLYVG GAPDFSKLAR AAAVSSGFDG AIQLVSLGGR QLLTPEHVLR QVDVTSFAGH  180
PCTRASGHPC LNGASCVPRE AAYVCLCPGG FSGPHCEKGL VEASAGDVDT LAFDGRTFVE  240
YLNAVTESEL ANEIPVEKAL QSNHFELSLR TEATQGLVLW SGKATERADY VALAIVDGHL  300
QLSYNLGSQP VVLRSTVPVN TNRWLRVVAH REQREGSLQV GNEAPVTGSS PLGATQLDTD  360
GALWLGGLPE LPVGPALPKA YGTGFVGCLR DVVVGRHPLH LLEDAVTKPE LRPCPTP     417
```

Fig. 7

```
LADFNGFSYL ELKGLHTFER DLGEKMALEM VFLARGPSGL LLYNGQKTDG KGDFVSLALH   60
NRHLEFRYDL GKGAAIIRSK EPIALGTWVR VFLERNGRKG ALQVGDGPRV LGESPVPHTM  120
LNLKEPLYVG GAPDFSKLAR GAAVASGFDG AIQLVSLRGH QLLTQEHVLR AVDVAPFAGH  180
PCTQAVDNPC LNGGSCIPRE ATYECLCPGG FSGLHCEKGI VEASVGDLET LAFDGRTYIE  240
YLNAVTESEL TNEIPAEKAL QSNHFELSLR TEATQGLVLW IGKVGERADY MALAIVDGHL  300
QLSYDLGSQP VVLRSTVKVN TNRWLRVRAH REHREGSLQV GNEAPVTGSS PLGATQLDTD  360
GALWLGGLQK LPVGQALPKA YGTGFVGCLR DVVVGHRQLH LLEDAVTKPE LRPCPTL     417
```

Fig. 8

```
LADFNGFSHL ELRGLHTFAR DLGEKMALEV VFLARGPSGL LLYNGQKTDG KGDFVSLALR   60
DRRLEFRYDL GKGAAVIRSR EPVTLGAWTR VSLERNGRKG ALRVGDGPRV LGESPKSRKV  120
PHTVLNLKEP LYVGGAPDFS KLARAAAVSS GFDGAIQLVS LGGRQLLTPE HVLRQVDVTS  180
FAGHPCTRAS GHPCLNGASC VPREAAYVCL CPGGFSGPHC EKGLVEASAG DVDTLAFDGR  240
TFVEYLNAVT ESEKALQSNH FELSLRTEAT QGLVLWSGKA TERADYVALA IVDGHLQLSY  300
NLGSQPVVLR STVPVNTNRW LRVVAHREQR EGSLQVGNEA PVTGSSPLGA TQLDTDGALW  360
LGGLPELPVG PALPKAYGTG FVGCLRDVVV GRHPLHLLED AVTKPELRPC PTP         413
```

Fig. 9

```
LADFNGFSYL ELKGLHTFER DLGEKMALEM VFLARGPSGL LLYNGQKTDG KGDFVSLALH   60
NRHLEFRYDL GKGAAIIRSK EPIALGTWVR VFLERNGRKG ALQVGDGPRV LGESPKSRKV  120
PHTMLNLKEP LYVGGAPDFS KLARGAAVAS GFDGAIQLVS LRGHQLLTQE HVLRAVDVAP  180
FAGHPCTQAV DNPCLNGGSC IPREATYECL CPGGFSGLHC EKGIVEASVG DLETLAFDGR  240
TYIEYLNAVT ESELTNEIPA EKALQSNHFE LSLRTEATQG LVLWIGKVGE RADYMALAIV  300
DGHLQLSYDL GSQPVVLRST VKVNTNRWLR VRAHREHREG SLQVGNEAPV TGSSPLGATQ  360
LDTDGALWLG GLQKLPVGQA LPKAYGTGFV GCLRDVVVGH RQLHLLEDAV TKPELRPCPT  420
L                                                                 421
```

Fig. 10

MODIFIED AGRIN-FRAGMENT CAPABLE OF RESTORING MUSCLE STRENGTH FOR USE AS A MEDICAMENT

BACKGROUND OF THE INVENTION

The invention refers to a modified agrin-fragment for use as a medicament. Additionally the invention refers to the use of the modified agrin-fragment for the manufacturing of a medicament for the treatment of different especially muscular or motor neuron diseases but also for the treatment of further neurotrypsin related diseases. Furthermore the invention refers to the use of the modified agrin-fragment in the treatment of different diseases. Finally the invention relates to a pharmaceutical composition comprising the modified agrin-fragment and to a special modified agrin fragment.

Aging people of 60 years or more face an inexorable decline of lean body mass. Because this is commonplace it was not held worthwhile to investigate the underlying mechanism for a long time. Currently the age-related decline in lean body mass are referred to as sarcopenia or frailty.

Sarcopenia and frailty are both highly relevant entities with regard to functionality and independence in the elderly. Sarcopenia is regarded as the degenerative age-related decline in muscle mass and strength leading at its late stage to frailty and disability. The muscle mass declining rate of sarcopenia patients is significantly faster than of people not affected with the disease. Sarcopenia is not a static condition but aggravating with aging. Because of its slow development, people usually are unaware of sarcopenia until having reached already an advanced stage.

Sarcopenic muscle mass is characterized by a continuously shrinking number of muscle fibers. The fiber size is more heterogeneous, and fiber type grouping is observed. Fiber type grouping is thought to be caused by repeated denervation/reinnervation. In addition, aged muscle is characterized by infiltration of fat and connective tissue. All this causes a decline in muscle strength and speed of movement. The age-related changes observed in many muscles are thought to be caused to some extent by age-related changes in the innervation of their muscle fibers. During aging a significant and progressive reduction in the estimated number of functioning motor units (MU) is observed. Similarly, an apparent muscle strength decline associated with a substantial loss of MUs is observed in individuals afflicted with motoneuron diseases such as amyotrophic lateral sclerosis (ALS) or less severe forms of spinal muscle atrophy (SMA).

Cycles of denervation/reinnervation of muscle fibers requires synaptic plasticity. The process of synaptic plasticity is not yet understood in detail. However, in the past years some key players in the formation and maintenance of neuromuscular junctions (NMJ's) were identified (Song and Balice-Gordon, 2008). The well characterized protein Agrin (Bezakova and Ruegg, 2003) plays a pivotal role in the synapse-formation process by assisting formation and maintenance of the postsynaptic apparatus of developing NMJs.

Agrin is a large heparan proteoglycan with a molecular weight of 400-600 kDa. (Database accession number NP_940978). The protein core consists of about 2000 amino acids and its mass is about 225 kDa. It is a multidomain protein composed of 9 K (kunitz-type) domains, 2 LE (laminin-EGF-like) domains, one SEA (sperm protein, enterokinase and agrin) domain, 4 EG (epidermal growth factor-like) domains and 3 LG (laminin globular) domains (FIG. 1). Agrin is a very important protein and agrin deficient mice die at birth due to respiratory failure. This is caused by the fact that agrin is strictly required for the proper innervation of muscle fibers and that these mice are not able to build proper NMJ's.

Agrin exists in several splice variants and can be expressed as a secreted protein, containing the N-terminal NtA (N-terminal agrin) domain, which is the most abundant form of agrin and the predominant form expressed in motor neurons. It is produced in the soma of the neurons, transported down the axon and released from the axon ending of the motor nerve into the synaptic cleft of the NMJ. Here it acts as an agonist of LRP4 and may also become a component of the basal lamina. In the CNS, most agrin is expressed as a type-II transmembrane protein by alternative splicing at the N-terminus lacking the N-terminal NtA domain (Bezakova and Ruegg, 2003).

The serine/threonine (S/T) rich segments in agrin are responsible for a high degree of glycosylation, containing several glycosylation and glucosaminoglycan attachment sites giving rise to the big mass of the proteoglucan. The C-terminal, 75 kDa moiety of agrin starting with the first EG domain is required for full activity in acetylcholine receptor (AChR) clustering activity on muscle cells, although the most C-terminal 20 kDa fragment is sufficient to induce AChR aggregation (Bezakova and Ruegg, 2003). Several binding sites for interaction partners of agrin, including α-dystroglycan, heparin, some integrins and LRP4 are mapped to the C-terminal region. The large heparansulfate side chains are binding sites for heparin binding proteins, e.g some growth factors.

In the C-terminal part of human agrin, there are 2 alternative splice sites y and z At the y-site, there may be inserts of 0, 4, 17 or 21 (4+17) amino acids and at the z site there may be inserts of 0, 8, 11 or 19 (8+11) amino acids. The function of the four inserted amino acids in the y-site is to create a heparin binding site. Motor neurons express predominantly y4 agrin. The most important splice site of agrin in respect of NMJ maturation is the z-site, giving agrin the ability to be active as an acetylcholine-receptor clustering agent. It is well known that full length agrin containing the insertion of 8 amino acids at the z-site in presence of the 4 amino acid insert in splice site y (y4z8) generates an agrin variant with a half maximal AChR clustering activity of 35 pM in cultured myotube clustering assays. The insertion of 11 amino acids give rise to a half maximal AChR clustering activity of 5 nM while the 19 amino acid insertion results in a half maximal AChR clustering activity of 110 pM. Agrin without an insertion at this site is not active in clustering acetylcholine-receptors on the in-vitro cultured myotubes (Bezakova and Ruegg, 2003). Thus, the most active form of agrin in the clustering assay is the y4z8 variant, which is expressed by motor neurons.

A ~40 kDa C-terminal fragment of agrin (y4z8) containing the LG2, EG4 and the LG3 domains was found to be active in AChR clustering with an EC50 of 130 pM in the AChR clustering activity while shorter fragments have only lower activities. The C-terminal LG3 domain with the z8 insertion exhibits a half maximal AChR clustering activity of only 13 nM, which is a factor 100 fold lower than the 40 kDa fragment (Bezakova and Ruegg, 2003).

During the development and maturation of the NMJ, agrin is a key player of molecules involved in the clustering of acetycholine-receptors. While NMJ's are destabilized by the neurotransmitter acetyl choline, agrin, which is secreted by the motor neuron, stabilizes and increases the clusters of the AChR's via phosphorylation of MuSK, a membrane bound receptor tyrosine kinase. The interaction of Agrin with MuSK is postulated to be mediated via LRP4, a low-density lipoprotein receptor (LDLR)-related protein. It was found that agrin (y4z8) has a ~10 fold higher affinity to LRP4 than agrin (y4z0) giving rise to the differential AChR clustering activity of the different agrin splice variants observed in the in-vitro cultured myotube assays. Upon agrin-binding, LRP4 causes self-phosphorylation of MuSK, which then activates the signal cascade for the expression and clustering of acetylcholine receptors.

Neurotrypsin is found in spinal cord extracts and is produced by motor neurons. Neurotrypsin is a secreted, trypsin like serine protease which is produced by CNS neurons, as well as by motor neurons (Stephan et al., 2008). Neurotrypsin consists of an N-terminal non catalytic part, containing a proline rich basic (PB) segment, a kringle (KR) domain, 4 scavenger receptor cysteine-rich (SRCR) domains, and a C-terminal protease domain (Gschwend et al., 1997). In human, a 4 bp deletion in exon 7 leads to a severe nonsyndromic mental retardation. The mutation leads to a truncated form of neurotrypsin lacking the protease domain, thus disabling the proteolytic function of the enzyme.

At present, agrin is the only known target of neurotrypsin. Neurotrypsin cleaves agrin at 2 distinct sites called α- and β-site. (FIG. 1). The α-site is located N-terminal from the SEA domain and the β-site is placed in front of the LG3 domain of agrin. Cleavage at the α-site generates a ~100 kDa C-terminal agrin fragment running at ~130 kDa in a 4-12% bis-tris SDS gel. Cleavage at the β-site liberates the C-terminal LG3 domain running at ~22 kDa in the gel (Molinari et al., 2002; Reif et al., 2007). All C-terminal fragments could be detected in brain extracts and spinal cord extracts of mice (Stephan et al., 2008). In neurotrypsin knock out mice, none of the fragments could be detected. As a consequence, neurotrypsin seems to be the only protease which cleaves agrin in significant amounts at the two cleavage sites. Cleavage of agrin by neurotrypsin contributes to neuromuscular plasticity and remodelling It was found that neurotrypsin (NT) overexpressing mice, so-called sarcopenia mice (muslik, M491S) (Stephan et al., 2008), show an early onset of sarcopenia. Detailed findings from systematic analysis of the sarcopenia mice demonstrate that a good correlation exists to human data. U.S. Ser. No. 12/007,928 gives a description of the animal model. Briefly the sarcopenia mice (muslik M491S) show:
 (i) that nerve fibres of mouse diaphragms grow towards the individual endplates,
 (ii) fragmented endplates on the diaphragm muscles, eventually leading to the disappearance of individual endplates, i.e. a loss of pre- and postsynaptic sites,
 (iii) reduced fibre number and decreased homogeneity of fibre size in mouse soleus muscles in neurotrypsin overexpressing animals. The sarcopenia mice has a reduced fibre number (about 30%) and an increased inhomogeneity of fibre sizes.

In WO 97/21811 it is proposed to use agrin or agrin fragments in methods of treatment of a disease that affects muscle. However, such attempts have up to date not shown to be successful The object of the present invention is to provide a therapy for different muscular disorders involving a reduction of functional NMJs and/or motor-units (MU).

SUMMARY OF THE INVENTION

In general the invention provides for novel engineered human or mouse agrin protein variants which are resistant to the proteolytic activity of neurotrypsin and serve as a biological therapeutic reagent for the treatment of humans suffering from sarcopenia or further neurotrypsin-related diseases. Resistance to the activity of neurotrypsin can e.g. achieved by modifying the cleavage sites, especially the β-cleavage site, of the agrin fragment accordingly or by deleting the cleavage sites from the fragment.

Investigations of the applicant have shown that in vivo activity of the agrin-fragment is mainly dependent on the presence of both domains LG2 and LG3 together. WO97/21811 showed in vitro activity for AChR-clustering for LG3 alone. However, no in vivo activity of LG3 could be shown. As it appears activation of LRP4 alone is not sufficient to achieve full in vivo activity.

So one important feature of the invention is that the domains LG2 and LG3 are not separated in vivo due to the activity of neurotrypsin. In order to avoid such separation the agrin-fragment used according to the invention has been modified such that it does not any more include the β-cleavage site of neurotrypsin in naturally occurring agrin present between domains LG2 and LG3.

The terms LG2 and LG3 if used in this application shall encompass all possible different splice variations of these domains as mentioned above. SEQ ID NO: 1 e.g shows the human sequence of domain LG2 with an insert of 4 amino-acids (SEQ ID NO: 5) at the y-site while SEQ ID NO: 2 shows the sequence of the domain LG3 with an insert of 8 amino-acids (SEQ ID NO: 8) at the z-site. In the domain LG2 as shown in SEQ ID NO: 1 the y-site is between proline 115 and valine 120. It is understood that the position of the valine may change depending on the length of the inserts at the y-splice site. In the domain LG3 as shown in SEQ ID No: 2 the z-site is between serine 19 and glutamic acid 28. Also here it is clear that the position of the glutamic acid may change depending on the length of the inserts at the z-splice site. Further examples for sequences of inserts at the mentioned splice-sites are given below.

As additionally variations of sequence are possible which do not affect the biological activity the invention shall not be limited to the indicated sequences of the different splice variants of the domains LG2 and LG3 but shall also encompass variants thereof having at least 90% preferably 95% identity.

The invention provides an agrin-fragment which at the same time has in vivo activity and which is not cleaved by neurotrypsin in vivo.

In vivo activity if used in this application shall encompass effects spanning from prevention of whole body weight loss and muscle strength loss to restoration of whole body weight and muscle strength in sarcopenia mice (muslik M491S).

The term agrin fragment if used in this application covers the secreted or transmembraneous form of agrin where the basic amino acids arginine and/or lysine in at least the recognition site β and possibly also in the site a for neurotrypsin are mutated to any other amino acid generating an at least partially neurotrypsin resistant form of agrin. It encompasses fragments which comprise at least the LG3 and LG2 domain of agrin but also fragments which additionally include at least one further domain naturally occurring in agrin, e.g. the LG1 and EG1-4 domains.

Alternatively the agrin fragment can be chemically modified in a way that prevents proteolytic cleavage by neurotrypsin or neurotrypsin like serine proteases.

Additionally agrin fragments falling under the invention are destined to contain any naturally or unnaturally inserted amino acids in the splice sites y and z.

In one embodiment the invention is directed to C-terminal agrin fragments containing at least the neurotrypsin β-cleavage site, wherein this cleavage site is modified in a way that neurotrypsin or neurotrypsin like proteases are unable to cleave it. An especially preferred modified agrin fragment referred to as neurotrypsin resistant C44 y4z8K/A comprises the amino acid sequence according to SEQ ID NO: 3 shown in FIG. 2B. The abbreviation K/A stands for the mutation of K (Lysine) to A (Alanine) in the β-cleavage site. Further preferred modified agrin fragments referred to as C44 y0z8K/A (human), C44 y0z8K/A (mouse), C44 y4z0K/A (human) and C44 y4z8K/A (mouse) comprise the amino acid sequences according to SEQ Ids NO: 11-14 shown in FIGS. 7-10.

Such agrin fragments can be obtained by usual recombinant engineering, as described in the examples for the agrin fragment C44 y4z8K/A. For their experiments the applicants used a fragment which was purified by using a His8 introduced at the N-terminus. The fragment, referred to in the text as C44K/A, has a sequence according to SEQ ID NO: 4.

The only difference between neurotrypsin resistant C44 y4z8K/A and C44K/A is that the latter protein additionally includes the His8-tag which was not removed prior to testing the fragment.

As is shown in the examples the modified agrin fragments according to the invention are able to induce muscle development in mice suffering from sarcopenia. So one important aspect of this invention is the use of the claimed agrin fragments as medication.

A further aspect of the invention is the use of the modified agrin fragment for the treatment, or for the manufacture of a medicament for the treatment of neuromuscular diseases or diseases of nerve, muscle and neuromuscular junctions, including, but not limited to, sarcopenia, muscle weakness, frailty, muscular atrophy and muscular dystrophy, myasthenia, myotonia, spinal muscular atrophy, amyotrophic lateral sclerosis, and primary lateral sclerosis.

Apart from the diseases mentioned the modified agrin fragment can be used in general in the treatment of all diseases which in which the neurotrypsin level is elevated due to e.g. overexpression.

A further aspect is the treatment of disuse atrophy of muscles (muscle atrophy), with loss of mass and strength, which can occur after prolonged immobility. Examples of prolonged immobility are extended bedrest, or having a body part, for instance a limb, in a cast, or mechanical ventilation in patients suffering from lung diseases. There are also many diseases and conditions which cause atrophy of muscle mass. For example diseases such as cancer and AIDS induce a body wasting syndrome called "cachexia", which is notable for the severe muscle atrophy seen. This type of atrophy can be reversed with exercise unless the condition is severe. It is know that disuse atrophy causes remodeling at the neuromuscular junction. The observed neuromuscular changes and plasticity are characteristic not only for aging (sarcopenic) NMJs but also for disuse atrophy.

The invention provides for a pharmaceutical composition containing a modified agrin fragment according to the invention in a pharmaceutically acceptable vehicle to treat sarcopenia and muscular diseases. Such a treatment may be combined with therapeutical approaches including active movement training or nutrition optimization.

It has turned out that one preferred mode of administration is subcutaneous injection. Preferably the pharmaceutical compositions therefor include carriers which allow such injection. However, it is also conceivable to administer the fragments intramuscularly or intravenously or intrathecally or orally or transdermally or transepithelial or intrapulmonary or intranasal. The following formulations or devices may be used: microencapsulation, microprojection liposomes, PEGylation or PEGlytated derivatives of agrin fragment, or nanoparticles. Also such pharmaceutical compositions are covered by the invention.

BRIEF DESCRIPTION OF THE DRAWINGS

FIG. 1: shows schematic representation of the domain structure of agrin.

FIG. 2A: is a schematic representation of neurotrypsin-resistant agrinC44

FIG. 2B: amino acid sequence of neurotrypsin-resistant agrin C44 y4z8 (SEQ ID NO: 3)

FIG. 7: amino acid sequence of neurotrypsin-resistant agrin C44 y0z8K/A (h) (SEQ ID NO: 11)

FIG. 8: amino acid sequence of neurotrypsin-resistant agrin C44 y0z8K/A (m) (SEQ ID NO: 12)

FIG. 9: amino acid sequence of neurotrypsin-resistant agrin C44 y4z0 (SEQ ID NO: 13)

FIG. 10: amino acid sequence of neurotrypsin-resistant agrin C44 y4z8K/A (m) (SEQ ID NO: 14)

FIG. 1 shows a schematic representation of agrin. Agrin has a core protein mass of approximately 225 kDa. It is a multidomain protein composed of 9 K (kunitz-type) domains, 2 LE (laminin-EGF-like) domains, one SEA (sperm protein, enterokinase and agrin) domain, 4 EG (epidermal growth factor-like) domains and 3 LG (laminin globular) domains. On both sides of the SEA domain a serine/threonine rich (S/T) region is found. Agrin exists in several isoforms. The secreted isoform contains a signal sequence (SS) which is cleaved off, followed by an N-terminal agrin domain (NtA). The type II transmembrane bound form contains a trnasmembrane (TM) region, directly followed by the first kunitz type domain. The C-terminal, 75 kDa moiety of agrin starting with the first EG domain is required for full activity in acetylcholine receptor (AChR) clustering activity on muscle cells, although the most C-terminal 20 kDa fragment is sufficient to induce AChR aggregation at low potency. Several binding sites for interaction partners of agrin, including α-dystroglycan, heparin, some integrins and LRP4 are mapped to the C-terminal region. The large heparansulfate side chains (lollipop chains) are binding sites for heparin binding proteins, e.g some growth factors. Lollipops indicate glycosylation sites. x, y, z assign the alternative splice sites in the C-terminal region of agrin. At the x-site (missing in chick and frog), there may be 0, 3 or 12 amino acids, at the y site there may be 0 or 4 amino acids and at the z site there may be 0, 8, 11 or 19 (8+11) amino acids inserted. "α- and β-cleavage" indicate the two conserved neurotrypsin cleavage sites. The rough protein core masses of proteolytic fragments after neurotrypsin cleavage are indicated above.

The abbreviations used in FIG. 1 have the following meaning: SS: signal sequence; NtA: N-terminal agrin domain; TM: transmembrane segment; K: kunitz type domain; LE: laminin EGF-like domain; S/T: serine/threonine rich segment; SEA: sperm protein, enterokinase and agrin domain; EG: epidermal growth factor-like domain; LG: laminin globular domain.

FIG. 2A shows a schematic representation of a modified agrin fragment used according to the invention. The fragment contains the C-terminal domains LG2, EG4 and LG3 of agrin. The β-cleavage site of neurotrypsin is deleted.

FIG. 2B shows the amino acid sequence (SEQ ID NO: 3) of the neurotrypsin resistant C44 y4z8K/A fragment of agrin. The fragment contains the C-terminal domains LG2, EG4 and LG3 of agrin. The β-cleavage site of neurotrypsin is deleted by the mutation of lysine to an alanine.

The abbreviations used in FIG. 2 have the following meaning: LG: laminin globular domain; EG: epidermal growth factor like domain; y and z indicate the alternative splice sites of agrin's C-terminal part. Striked out β-cleavage: mutation at the β-cleavage site for neurotrypsin rendering the neurotrypsin resistant agrin fragment.

Figure 3:
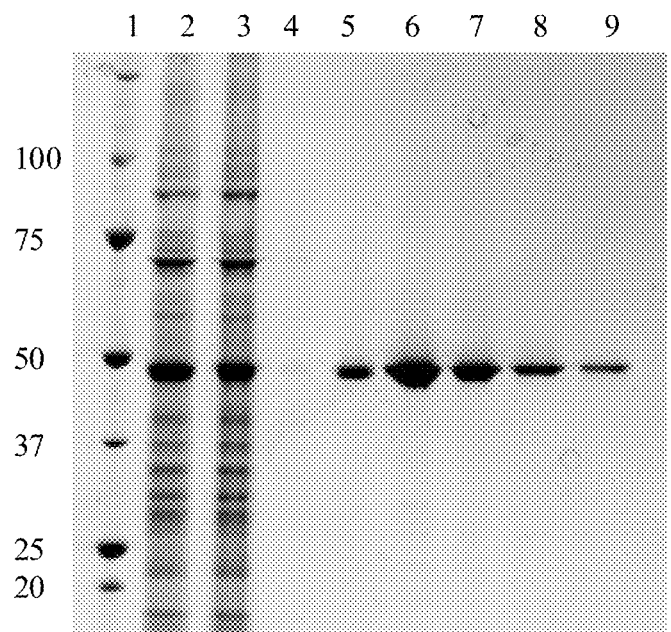
FIG. 3: is the representation of a SDS-PAGE gel showing the purification of C44K/A (SEQ ID NO: 4) via IMAC.

FIG. 3 is a Sypro ruby stained SDS-PAGE gel showing the purification progress of C44K/A in immobilized metal affinity chromatography. Culture supernatant from HEK 293 cells transfected with a pEAK8 vector containing the gene for C44K/A was loaded on a 10 ml IMAC column labeled with $Ni^{2+}$. After washing the column with appropriate buffer, the bound protein was eluted with buffer containing 500 mM imidazol (5-9). Lane 1: Biorad Prescission plus protein marker; Lane 2: concentrated culture supernatant; Lane 3: flow through fractions;

Lane 4: wash fraction; Lanes 5-9: elution fractions

Figure 4:
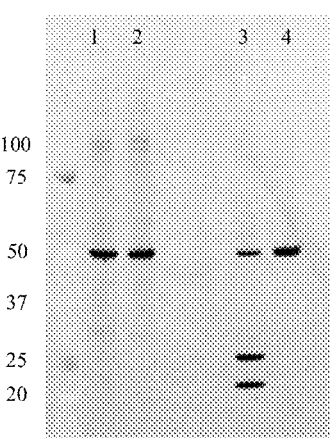
FIG. 4: is the representation of a SDS-PAGE gel showing the limited proteolytic digestion of C44K/A and human agrinC44 y4z8 with human neurotrypsin.

FIG. 4 is a Sypro ruby stained SDS-PAGE gel demonstrating the proteolytic digestion of C44K/A and human agrinC44 y4z8 with human neurotrypsin. C44K/A or human agrinC44 y4z8 were incubated with human neurotrypsin for 3.5 h at 37° C. (1+3) and subsequently subjected to SDS-PAGE. As control, the agrin fragments were incubated with buffer at the same conditions (2+4). The mutation K to A in the β-cleavage site efficiently abolishes a cleavage of the agrin fragment. Lane 1: C44K/A with addition of human neurotrypsin; Lane 2: C44K/A without the addition of human neurotrypsin; Lane 3: human agrinC44 y4z8 with the addition of human neurotrypsin; Lane 4: human agrinC44 y4z8 without the addition of human neurotrypsin.

Figure 5:
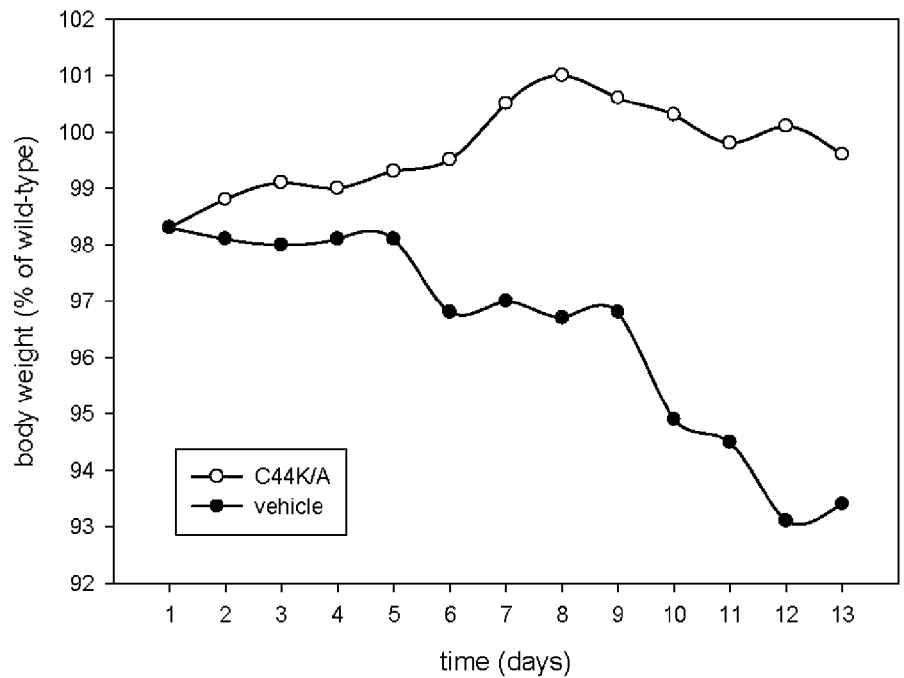
FIG. 5: is a graph showing the development of body weight of mice treated with C44K/A or vehicle.

FIG. 5 demonstrates the development of total body weights for sarcopenia mice (491S) treated with vehicle or C44K/A and wild type littermates treated with vehicle (wild type vehicle). The weight of the mice was determined every day throughout the whole duration of the experiment until day 22. The weight of the mice is expressed as percentage of the wild type littermates treated with vehicle. Treatment started at day 1 and stopped at day 13. Grip strength was measured at day 13.

Figures 6A, 6B:
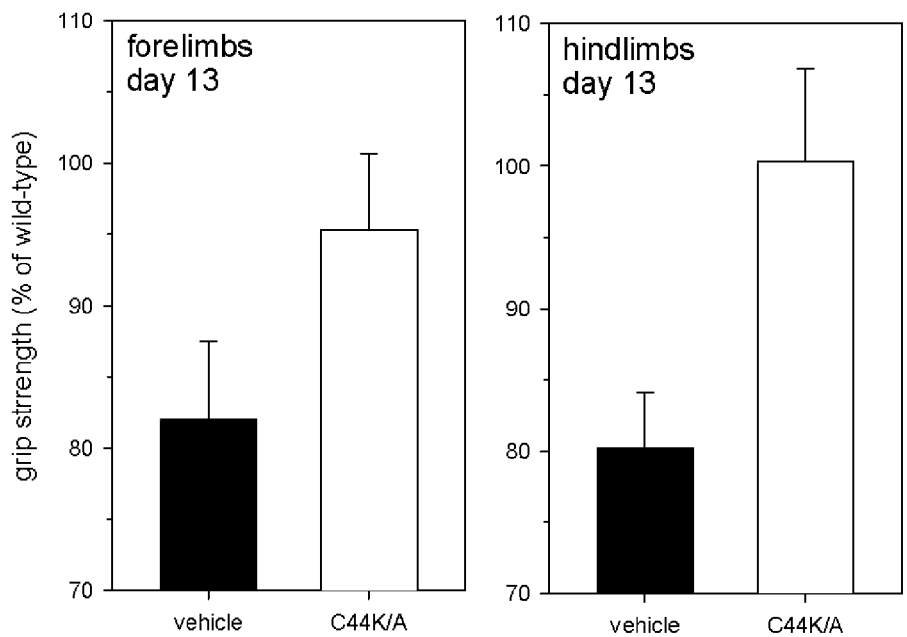
FIGS. 6A,B: show the fore-limb and hind-limb grip strength at day 13 of the experiment in WILD TYPE littermate mice and sarcopenia mice treated with C44K/A or vehicle.

FIGS. 6A and 6B show the fore-limb and hind-limb grip strength for sarcopenia mice treated with vehicle (vehicle) or C44K/A (C44K/A). The grip strength is measured at day 13. Grip strength of different treatment groups is indicated as percentage of vehicle treated wild type littermate mice. Standard deviations are indicated as error bars. (N=5 for each group).

FIG. 7 shows the amino acid sequence of neurotrypsin-resistant human agrin C44 y0z8K/A (h) (SEQ ID NO: 11).

FIG. 8: shows the amino acid sequence of neurotrypsin-resistant mouse agrin C44 y0z8K/A (m) (SEQ ID NO: 12)

FIG. 9 shows the amino acid sequence of neurotrypsin-resistant human agrin C44 y4z0K/A (SEQ ID NO: 13)

FIG. 10 shows the amino acid sequence of neurotrypsin-resistant mouse agrin C44 y4z8K/A (m) (SEQ ID NO: 14).

All fragments shown in FIGS. 7-10 contain the C-terminal domains LG2, EG4 and LG3 of agrin. The β-cleavage site of neurotrypsin is deleted by the mutation of lysine to an alanine.

Figure 11:
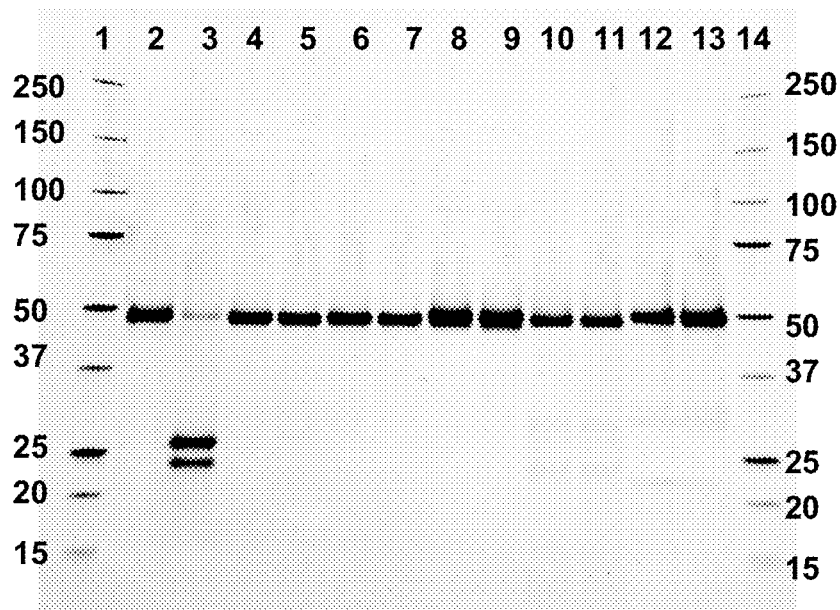
FIG. 11: is the representation of a SDS-PAGE gel showing the limited proteolytic digestion of C44K/A fragments.

FIG. 11 is a Sypro ruby stained SDS-PAGE gel demonstrating the proteolytic digestion of further C44-fragments in an neurotrypsin assay. The different C44-fragments shown in FIGS. 7-10 andr human agrin C44 y4z8K/A (FIG. 2B) were incubated in assays with (hNT+) and without human neurotrypsin (hNT−) for 3.5 h at 37° C. and subsequently subjected to SDS-PAGE. As control a precission marker and human Agrin C44y0z0 without mutation in the β-cleavage site was incubated at the same conditions. Again it is apparent that the mutation K to A in the β-cleavage site efficiently abolishes a cleavage of the mutated agrin fragments by neurotrypsin. Lane 1: precission marker; Lane 2: C44 y0z0 without mutation (hNT−); Lane 3: C44 y0z0 without mutation (hNT+); Lane 4: human agrinC44 y4z0K/A (hNT−); Lane 5: human agrinC44 y4z0K/A (hNT+); Lane 6: human agrinC44 y0z8K/A (hNT−); Lane 7: human agrinC44 y0z8K/A (hNT+); Lane 8: mouse agrinC44 y0z8K/A (hNT−); Lane 9: mouse agrinC44 y0z8K/A (hNT+); Lane 10: human agrinC44 y4z8 (hNT−); Lane 11: human agrinC44 y4z8 (hNT+); Lane 12: mouse agrinC44 y4z8K/A (hNT−) Lane 13: mouse agrinC44 y4z8K/A (hNT+).

Figure 12:
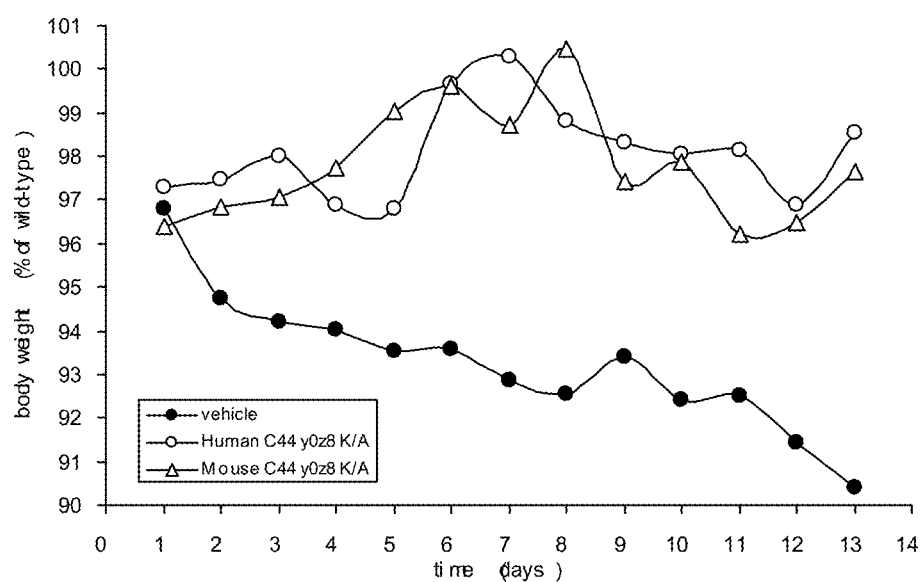
FIG. 12: demonstrates the development of total body weights for sarcopenia mice (491S) treated with vehicle (vehicle) or human C44K/A (0.8) or mouse C44K/A (0.8) and wild type littermates treated with vehicle (wild type vehicle).

FIG. 12 demonstrates the development of total body weights for sarcopenia mice (491S) treated with vehicle (vehicle) or human C44 y0z8K/A or mouse C44 y0z8K/A and wild type littermates treated with vehicle (wild type vehicle). The weight of the mice was determined every day throughout the whole duration of the experiment until day 22. The weight of the mice is expressed as percentage of the wild type littermates treated with vehicle. Treatment started at day 1 and stopped at day 13.

Figure 13A:
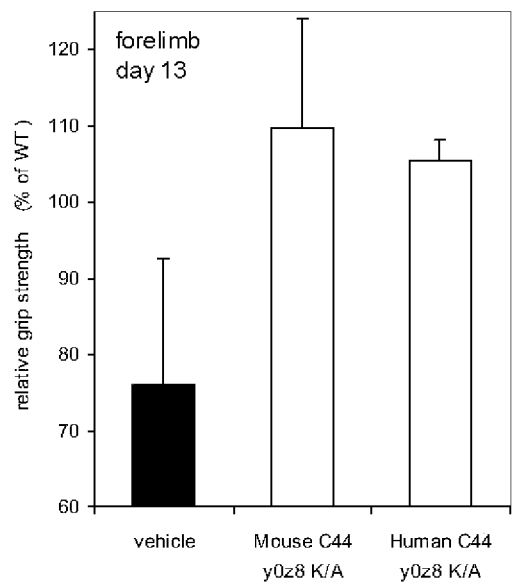
FIG. 13A,B: show the fore-limb and hind-limb grip strength for sarcopenia mice treated with vehicle (vehicle) or human C44K/A (0.8) or mouse C44K/A (0.8) and wild type littermates treated with vehicle (wild type vehicle).
Figure 13B:
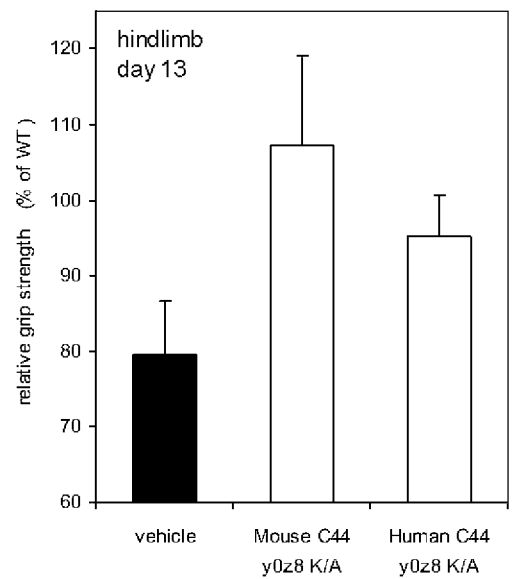

FIGS. 13A and 13B show the fore-limb and hind-limb grip strength for sarcopenia mice treated with vehicle (vehicle) or human C44 y0z8K/A or mouse C44 y0z8K/A and wild type littermates treated with vehicle (wild type vehicle). The grip strength is measured at day 13. Grip strength of different treatment groups is indicated as percentage of vehicle treated wild type littermate mice. Standard deviations are indicated as error bars. (N=5 for each group).

DETAILED DESCRIPTION OF THE INVENTION

The applicants were the first to show that sarcopenia mice in addition to the known deficiencies also have a decline of lean body mass (FIG. 5) and reduced grip strength compared to healthy wild type mice (FIG. 6).

Starting from this fact the applicants were able to show that neurotrypsin resistant agrinC44K/A as shown in e.g. FIG. 2 *a* and comprising the sequence as shown in FIG. 2 *b* is able to increase the weight- and grip strength of sarcopenia mice, i.e. neurotrypsin overexpressing mice as shown in FIGS. 5; 6A, B.

The restoring effect is achieved after subcutaneous administration of C44K/A-fragments. The effect is not locally limited to the site of injection but has a beneficial effect on total body mass and muscle strength. The treated sarcopenia mice are stronger and have increased grip strength in both fore and hind limb.

Administration of C44K/A will also facilitate the re-innervation of muscle fibers at ectopic AChR clusters and lead to a stabilization and maturation of the newly formed NMJ. Thus, administration of C44K/A will also be beneficial in rehabilitation processes where re-innervation of muscle fibers or muscles is needed.

In contrast to the herein claimed neurotrypsin-resistant human agrin, agrin fragments having intact cleavage sites for neurotrypsin (as described in WO 97/21811) will not be beneficial as they are rapidly degraded by neurotrypsin and will loose their AChR clustering activity.

Agrin is cleaved by neurotrypsin (FIG. 1) at two sites. The α-cleavage site is located between arginine 1102 (R1102) and alanine 1103 (A1103). The β-cleavage site is located between lysine 1859 (K1859) and serine 1860 (S1860; numbering corresponding to human agrin NP_940978). Agrin cleavage by neurotrypsin at the β-site generates a fragment of approximately 20 kDa (agrinC22) ranging from S1860 to the C-terminus.

Neurotrypsin-resistant human agrin used according to the invention is a C-terminal agrin fragment consisting of the LG2, EG4 and LG3 domain of agrin and harbours the inactivated β-cleavage site of neurotrypsin. Its P1 lysine residue (K1859) is mutated to an alanine which causes that neurotrypsin is no longer able to cleave agrin at this site (FIG. 3).

Neurotrypsin-resistant human agrinC44 y4z8 as defined in the present invention is the 44 kDa C-terminal agrin fragment of SEQ ID NO: 3 where the basic amino acid lysine-1859 (NP_940978) (or lysine 227 in SEQ ID NO: 3) is mutated to an alanine resulting in an agrin fragment, which is not cleavable by neurotrypsin. This fragment may further contain no insertion at the y site located between amino acids P1751 and V1752 (NP_940978) or no insertion or the 8, 11 or 19 amino acids insertions at the z-site located between amino acids S1884 and E1885 (NP_940978), or combinations therof. The inserted sequences at the y-site may be KSRK (y4, SEQ ID NO: 5), VLSASHPLTVSGASTPR (y17, SEQ ID NO: 6) and KSRKVLSASHPLTVSGASTPR (y21, SEQ ID NO: 7) and at the z-site ELANEIPV (z8, SEQ ID NO: 8), PETLDSGALHS (z11, SEQ ID NO: 9) or ELANEIPVPETLDSGALHS (z19, SEQ ID NO: 10, a combination of SEQ ID NO: 8 and SEQ ID NO: 9).

If in this application it is reffered to human agrin C44 y4z8, such agrin fragment shall correspond to the fragment shown in SEQ ID NO: 3 with the only difference that alanine in position 227 of the shown sequence is replaced by a lysine in human agrin C44 y4z8.

In the present invention, the term "neurotrypsin-resistant human agrin C44 y4z8" also comprises agrin variants of the protein defined by SEQ ID NO: 3 where no insertion is introduced in the y-site (i.e., C44 y0z8), or no insertion is introduced in the z-site (i.e., C44 y4z0), or where instead of the 8 amino acid insertion a 11 or 19 amino acid insertion corresponding to SEQ ID NO: 9 and SEQ ID NO: 10 is inserted in the z-site (i.e., C44 y4z11; and C44 y4z19). This includes also all possible combinations of variants generated by introducing the possible amino acids in the y- and z-site. One such variant, for example, is shown in SEQ ID NO: 15, which corresponds to neurotrypsin-resistant human agrin C44 y0z19. Neurotrypsin-resistant mouse agrin C44 y0z19 is shown in SEQ ID NO: 16.

The term "neurotrypsin-resistant human agrinC44 y4z8" also includes agrin fragments of SEQ ID NO: 3 which contains additional amino acids at the N-terminus or C-terminus. Such additional amino acids at the N-terminus are e.g. present due to the method of preparation by recombinant synthesis and expression in suitable cells. An example of such a protein falling under the definition of "neurotrypsin-resistant human agrinC44 y4z8" is the protein C44K/A SEQ ID NO: 4 prepared according to EXAMPLE 1, which contains an His8 tag with a prescission protease cleavage site to simplify purification (FIG. 4).

Proteins not capable of being cleaved by neurotrypsin containing elongations at the N-terminus by one or more domains of agrin up to the natural N-terminaus of agrin are also included, as well as glycosylated or in other ways post-translationally, enzymatically or chemically modified protein variants of neurotrypsin-resistant human agrin.

As shown in the examples neurotrypsin-resistant human agrinC44 y4z8 has the ability to restore the sarcopenic phenotype caused by the overexpression of neurotrypsin.

As the unnatural high secretion of neurotrypsin by the motor nerve causes the over-digestion of agrin complexed to LRP4, a proper signalling to induce AChR clustering via MuSK is abolished. This leads to a loss of the NMJ and subsequently to a loss of the corresponding muscle fiber and to sarcopenia. Neurotrypsin-resistant human agrinC44 y4z8 is able to serve as an agonist for LRP4, stimulating the MuSK pathway. As no cleavage by neurotrypsin can occur, the complex remains stable and signaling is maintained during a long period. This leads to the expression of AChR's and the maintenance of the NMJ. Neurotrypsin-resistant human agrinC44 y4z8 is valuable for the treatment of sarcopenia caused by an access of neurotrypsin and may also help in diseases where a general destabilization of the NMJ is recognized.

The new mechanism underlying the effectiveness of neurotrypsin-resistant human agrinC44 y4z8 for the treatment of sarcopenia is the therapy of a nerve derived maladjustment and not the attempt to influence the metabolism of the muscle fibers or the whole muscle.

The invention also relates to the use of neurotrypsin-resistant human agrin for the rehabilitative treatment after spinal cord injury, for example for the enhancement of use-dependent therapies. Such therapies can be enhanced by neurotrypsin-resistant human agrinC44 y4z8 due to its ability to promote AChR clustering, maintaining intact NMJ's or promoting the attachment of outgrowing nerve terminals to preformed ectopic AChR clusters on the muscle fiber, facilitating the generation of new NMJ's required for movements.

Further described is the production of neurotrypsin-resistant human agrinC44 y4z8 wherein a DNA coding for neurotrypsin-resistant human agrinC44 y4z8 is expressed in suitable expression systems and the resulting protein is subsequently purified. Several prokaryotic and eukaryotic expression systems are suitable for the production and secretion of neurotrypsin-resistant human agrinC44 y4z8. Prokaryotic expression systems include, but are not limited to, expression in *E. coli*. Eukaryotic expression systems include expression in mouse myeloma cells, baculovirus-mediated expression in insect cells, as well as expression in human embryonic kidney (HEK) cells, transient expression in Chinese hamster ovary (CHO) cells and stable expression in *Pichia pastoris*. These systems have the advantage that they can easily be adapted to serum-free conditions to reduce the amount of contaminating proteins in the supernatant and can be adapted for large scale production. In addition, a variety of cell lines may be used, including HEK293T and HEK293-cells, COS cells, CHO cells, HeLa cells, H9 cells, Jurkat cells, NIH3T3 cells, C127 cells, CV1 cells, CAP cells or SF cells.

For the purification of neurotrypsin-resistant human agrinC44 y4z8 standard protein purification technologies are applied. His-tagged protein can be purified using IMAC, but ion exchange chromatography or affinity purification using a heparin column can be used as well. Purification via an antibody raised against the C-terminal part of agrin can also be used. The eluted protein can then further be purified using a hydroxyapatite column or by gel filtration.

The following examples illustrate the invention, but are not limited to it. The skilled person in the field reading these examples will be able to apply other related conditions and these are also within the scope of the invention.

EXAMPLES

Example 1

Cloning of Neurotrypsin-Resistant Human 44-kd C-Terminal Fragment of Agrin (C44K/A)

Initially, full length human agrin y0z0 but lacking the N-terminal NtA domain (Human agrin y0z0 deltaNTA starts at position K156 in the protein sequence of accession number NP_940978) was cloned by PCR into the pEAK8 vector containing the coding sequence for the secretion signal of human calsyntenin-1, (Reif et al., 2007) via appropriate restriction sites and primers As template for human agrin the vector pCMV-XL5-Agrin (purchased from Origene USA) was used.

In two subsequently steps, the corresponding codons required for the y4z8 insertions were introduced by site directed mutagenesis using standard techniques resulting in the pEAK8 vector containing full length human agrin y4z8 deltaNtA.

Using this vector as template, the gene coding for the 44-kd C-terminal fragment of human agrin was amplified introducing the coding region for a His8 tag and a prescission protease cleavage site at the N-terminus of the translated protein.

The neurotrypsin-resistant form of human Agrin C44K/A was generated in a quick change mutagenesis step using primers which introduce the codon for an alanine at the place of the codon for the lysine in the cleavage site-β of agrin.

This plasmid generates a protein with the sequence of SEQ ID NO: 4 in the culture supernatant of transfected cells (without signal sequence) with the amino acids of the agrin moiety starting with leucine 21

Example 2

Expression and Purification of Human Agrin C44 and Neurotrypsin-Resistant C44K/A 500 ml HEK 293 cells grown in Excell 293 medium to a density of $1 \times 10^6$ cells/ml were pelleted by centrifugation in a Sorvall RC5C centrifunge at 100×g for 30 min. The cells were resuspended in 500 ml RPMI1640 medium prewarmed to 37° C. 1.25 mg of pEAK8 containing the insert for the expression of neurotrypsin-resistant humanAgrinC44 y4z8 were diluted in 25 ml 150 mM NaCl. 3.75 mg polyethylene imine (PEI), 25 kDa, were diluted in 25 ml 150 mM NaCl. Both solutions were pooled and incubated at room temperature for 10 min. Afterwards this solution was added to the cell suspension which was transferred to a 1000 ml spinner flask. The cell suspension was incubated for 7 days at 75 rpm on a stirring platform placed in an incubator with 5% $CO_2$ and 37° C. in humidified atmosphere.

After 7 days, the culture supernatant was harvested by centrifugation at 5000 rpm in a Sorvall RC5C centrifuge. Remaining particles were removed by filtration through a 0.22 um Millipore sterile filtration device. The filtrated culture supernatant was concentrated 10 times using a Pellicon PLCGC 10 kDa cuttoff tangential flow cartridge and dialyzed at least 1:1000 against 20 mM MOPS pH 8.5, 400 mM NaCl. The dialysate was subjected to immobilized metal affinity chromatography (IMAC) taking advantage of the His8 tag using a 10 ml bench top His Select column labeled with $Ni^{2+}$.

After loading of the concentrated and dialyzed cell culture supernatant, the column was washed with 100 ml dialysis buffer and bound protein was eluted with 5 times 10 ml of dialysis buffer containing 500 mM imidazole. The purification success was followed by SDS-PAGE (FIG. D). Positive fractions were pooled and concentrated 10 times with an AMICON 30 kDa cuttoff filtration device at 3000×g in a Sigma 4K15 centrifuge and dialysed 1:10000 against 20 mM MOPS pH 8.5, 200 mM NaCl. The concentration of the purified C44K/A was determined via UV spectroscopy using the extinction coefficient of 0.725 $cm^2$/mg.

Example 3

Removal of the His8 Tag by Prescission Protease Cleavage

In case the His8 tag should be removed, the buffer of 0.5 ml protein solution was exchanged to 50 mM Tris-HCL, pH 7.2, 150 mM NaCl, 1 mM DTT, 1 mM $Na_2$EDTA using a NAP-5 column pre-equilibrated with that buffer. The protein solution was eluted in 1 ml of the same buffer. 1 ul 1M DTT was added to the protein solution and mixed by flipping the tube several times. 20 ul of Prescission protease (1 U/ul) was added and the tube was mixed by flipping it several times. The reaction was done overnight at 4° C. A 0.5 ml gravity flow glutathione sepharose column was equilibrated with 5 ml PBS supplemented with 1 mM DTT. The digested protein solution was loaded and the flow through collected. The column was washed with 3 times 1 ml PBS supplemented with 1 mM DTT and the flow through was collected in the same tube as the previous flow through fraction. The collected flow-through fractions were dialysed 2 times 2 hours against 5 l of 20 mM MOPS pH 8.5, 400 mM NaCl to remove DTT and EDTA.

To remove the cleaved His8 tag a second IMAC was performed. A 1 ml Chelating sepharose FF column previously labelled with $Ni^{2+}$ ions was equilibrated with 5 ml 20 mM MOPS pH 8.5, 400 mM NaCl. The dialysed protein solution was applied onto the column and the flow through collected. The column was washed with 3 times with 1 ml 20 mM MOPS pH 8.5, 400 mM NaCl and the flow though collected in the same tube. The pooled fractions were concentrated with a AMICON 30 kDa cutoff concentrator to 0.5 ml. and the buffer was exchanged using a NAP-5 column pre-equilibrated with 20 mM MOPS pH 8.5, 200 mM NaCl. The concentration was determined via UV spectroscopy using the extinction coefficient of 0.725 $cm^2$/mg. The protein was freshly used for further experiments or stored at −80° C. until usage. The protein sequence of the corresponding protein corresponds to the portion of SEQ ID NO: 3 starting from Glycin 19.

Example 4

In Vitro Digestion of C44 and C44K/A by Human Neurotrypsin a) To demonstrate that neurotrypsin is not able to digest neurotrypsin-resistant human agrinC44 y4z8K/A, the protein was subjected to a neurotrypsin assay. As a control, human agrinC44 y4z8 was used. The agrinC44 substrates were used in concentrations of 1 uM in the assay and human neurotrypsin was added. The reaction was performed in 20 mM MOPS pH 8.3, 150 mM NaCl, 5 mM $CaCl_2$, 0.1% PEG 6000. Digestion was done for 6 h at 37° C. The setups were loaded on a 4-12% NuPAGE SDS gel and stained with Sypro ruby (FIG. 4).

b) In a further assay similar to a) it was shown that the C44K/A-fragments as shown in the FIGS. 2B and 7-10 are not digested by neurotrypsin (FIG. 11)

Example 5

Administration of Neurotrypsin-Resistant Human C44K/A in Mice

The sarcopenia mouse model used in the experiment are thy-1 driven neurotrypsin-overexpressors in C57BL/6NCRL background, (Stephan et al., 2008) and their wild type littermates. Both male and female animals were included, as in young mice at this age there are no differences in weight and muscle strength between sexes. The mice entered the experiment at P8 (eight days after birth).

Three groups with 3 mice per group were used: 1. Vehicle treated wild type mice 2. sarcopenia mice (M491S) treated with C44K/A 3. Vehicle treated sarcopenia mice.

The mice are injected subcutaneously with C44K/A or vehicle with a total dose of 6.4 mg/kg/day. Dosing started on day 1 and lasted until day 13. For all mice in the experiment the weight was measured once every day. The weight is averaged for each treatment group and plotted for every experimental day (FIG. 5). At the start of the experiment a slight reduction of body weight is already seen in the sarcopenia mice. Treatment of sarcopenia with C44K/A led to a significant increase in weight compared to vehicle treated mice. The sarcopenia mice treated with C44K/A recovered completely and further the same development as was observed in wild type littermates. In humans frail patients suffer from a weight loss of more than 5 kg per year (Bauer and Sieber, 2008; Lauretani et al., 2003). This corresponds to a loss of about 7% of total body weight. Sarcopenia mice treated with vehicle control showed markedly reduced body weights. During the experiment the sarcopenia mice experienced a weight loss of about 5%.

Example 6

Measurement of Grip Strength

At day 13 of the experiment described in example 5 Forelimb and Hindlimb grip strength were measured with a digital force meter (Columbus Instruments, Columbus Ohio) that retains applied peak force by precision force gauges. The force meter is fixed to a solid base and connected with a force transducer to a triangular shaped pulling bar, diameter approx. 1 mm. Data was collected on-line through a RS232 connection with a computer, stored in a .dat file by Grip Strength Meter software (Columbus Instruments) and transferred to excel for data management and statistical analysis. Grams (g) were used as unit for measurement of maximal force. Before measurement the mice are transferred to the experiment room and allowed to accustom for 10 min. Each mouse was allowed to grasp a metal bar, with a diameter of approximately 3 mm with its forepaws. Subsequently, the mouse was approached to the pulling bar facing away from the force meter and allowed to grasp the wire of the pulling bar with its forepaws or hindpaws. The mouse was pulled by its tail, in parallel to the pulling bar, towards the force meter, with a speed of approximately 10 cm/sec.

The pull was kept at constant speed until the forelimb respectively hindlimbs of the mouse released. An experimental session consisted of 5 trials for hindlimb grip strength. Between the trials the mice were allowed a resting period of ~1 minute. At least one day before actual experimental session the mice were trained with the described procedure. Each experimental session was done in a blinded fashion to avoid unwanted experimental bias.

The data were analyzed in the following way: For each mouse the highest and lowest values were excluded and the remaining 3 values were averaged. Subsequently, the data was averaged for each treatment group and normalized to vehicle treated wild type group At day 13 vehicle treated sarcopenia mice have lost about 20% of muscle strength compared to wild type whereas the C44K/A treated mice have similar grip strength to vehicle treated wild type.

For humans the decrease of muscle strength is approximately 20-40% when adults around 20 years of age are compared to individuals around age 70 and it may increase to above 50% when compared to individuals in their nineties (Bauer and Sieber, 2008; Lauretani et al., 2003). In this example the applicants demonstrates that a reduction of grip strength 20% is about 14 day was prevented.

This is the first time that a fragment of agrin has been shown to be active in vivo. After subcutaneous administration the protein C44K/A distributes in the body and exerted an beneficial effect to mice suffering from Sarcopenia like symptoms

Example 7

Administration of Neurotrypsin-Resistant Human C44 y0z8K/A and (Mouse-AgrinC44 y0z8K/A) in Mice The sarcopenia mouse model used in the experiment again (as in Example 5) are Thy-1 driven neurotrypsin-overexpressors in C57BL/6NCRL background, (Stephan et al., 2008) and their wild type littermates. Both male and female animals were included, as in young mice at this age there are no differences in weight and muscle strength between sexes. The mice entered the experiment at P8 (eight days after birth).

Four groups with 4 mice per group were used: 1. Vehicle treated wild type mice; 2. sarcopenia mice (M491S) treated with C44K/A(0,8); 3. sarcopenia mice (M491S) treated with mouse-AgrinC44(0,8)K/A; 4. vehicle treated sarcopenia mice.

The mice are injected subcutaneously with a total dose of 20 mg/kg/day. Dosing started on day 1 and lasted until day 13. For all mice in the experiment the weight was measured once every day. The weight is averaged for each treatment group and plotted for every experimental day. The relative weight in percentages compared to vehicle treated wild-type is given for each treatment group (FIG. 12). Treatment of sarcopenia mice with human C44y0z8K/A or mouse C44y0z8K/A led to a significant increase in weight compared to vehicle treated sarcopenia mice. The sarcopenia mice treated with C44y0z8K/A recovered completely and further the same development as was observed in wild type littermates. In humans frail patients suffer from a weight loss of more than 5 kg per year (Bauer and Sieber, 2008; Lauretani et al., 2003). This corresponds to a loss of about 7% of total body weight. Sarcopenia mice treated with vehicle control showed markedly reduced body weights. During the experiment the sarcopenia mice experienced a weight loss of about 5%.

Example 8

Measurement of Grip Strength

Measurement was done as described in Example 6.

FIGS. 13A and 13B show the fore-limb and hind-limb grip strength for sarcopenia mice treated with vehicle (vehicle) or human C44y0z8K/A or mouse C44y0z8K/A and wild type littermates treated with vehicle (wild type vehicle). The grip strength is measured at day 13. Grip strength of different treatment groups is indicated as percentage of vehicle treated wild type littermate mice. Standard deviations are indicated as error bars. (N=5 for each group).

The invention claimed is:

1. A modified agrin fragment having in vivo activity, comprising at least the domains LG2 and LG3 of human agrin in covalently interlinked form and modified in such a way that the fragment cannot be cleaved by neurotrypsin, wherein the modified agrin fragment comprises SEQ ID NO:11 (C44v0z8K/A variant).

2. A pharmaceutical composition comprising the modified agrin fragment according to claim 1 and a pharmaceutically acceptable carrier.

3. A modified agrin fragment having in vivo activity, comprising at least the domains LG2 and LG3 of mouse agrin in covalently interlinked form and modified in such a way that the fragment cannot be cleaved by neurotrypsin, wherein the modified agrin fragment comprises SEQ ID NO:12 (C44y0z8K/A variant).

4. A pharmaceutical composition comprising the modified agrin fragment according to claim 3 and a pharmaceutically acceptable carrier.

5. A modified agrin fragment having in vivo activity, comprising at least the domains LG2 and LG3 of human agrin in covalently interlinked form and modified in such a way that the fragment cannot be cleaved by neurotrypsin, wherein the modified agrin fragment comprises SEQ ID NO:3 (C44y4z8K/A variant).

6. A pharmaceutical composition comprising the modified agrin fragment according to claim 5 and a pharmaceutically acceptable carrier.

7. A modified agrin fragment having in vivo activity, comprising at least the domains LG2 and LG3 of mouse agrin in covalently interlinked form and modified in such a way that the fragment cannot be cleaved by neurotrypsin, wherein the modified agrin fragment comprises SEQ ID NO:14 (C44y4z8K/A variant).

8. A pharmaceutical composition comprising the modified agrin fragment according to claim 7 and a pharmaceutically acceptable carrier.

9. A modified agrin fragment having in vivo activity, comprising at least the domains LG2 and LG3 of human agrin in covalently interlinked form and modified in such a way that the fragment cannot be cleaved by neurotrypsin, wherein the modified agrin fragment comprises SEQ ID NO:15 (C44y0z19K/A variant).

10. A pharmaceutical composition comprising the modified agrin fragment according to claim 9 and a pharmaceutically acceptable carrier.

11. A modified agrin fragment having in vivo activity, comprising at least the domains LG2 and LG3 of mouse agrin in covalently interlinked form and modified in such a way that the fragment cannot be cleaved by neurotrypsin, wherein the modified agrin fragment comprises SEQ ID NO:16 (C44y0z19K/A variant).

12. A pharmaceutical composition comprising the modified agrin fragment according to claim 11 and a pharmaceutically acceptable carrier.

* * * * *

SEQUENCE LISTING

<160> NUMBER OF SEQ ID NOS: 16

<210> SEQ ID NO 1
<211> LENGTH: 184
<212> TYPE: PRT
<213> ORGANISM: Homo sapiens

<400> SEQUENCE: 1

Leu Ala Asp Phe Asn Gly Phe Ser His Leu Glu Leu Arg Gly Leu His
1               5                   10                  15

Thr Phe Ala Arg Asp Leu Gly Glu Lys Met Ala Leu Glu Val Val Phe
            20                  25                  30

Leu Ala Arg Gly Pro Ser Gly Leu Leu Tyr Asn Gly Gln Lys Thr
        35                  40                  45

Asp Gly Lys Gly Asp Phe Val Ser Leu Ala Leu Arg Asp Arg Leu
    50                  55                  60

Glu Phe Arg Tyr Asp Leu Gly Lys Gly Ala Ala Val Ile Arg Ser Arg
65                  70                  75                  80

Glu Pro Val Thr Leu Gly Ala Trp Thr Arg Val Ser Leu Glu Arg Asn
            85                  90                  95

Gly Arg Lys Gly Ala Leu Arg Val Gly Asp Gly Pro Arg Val Leu Gly
            100                 105                 110

Glu Ser Pro Lys Ser Arg Lys Val Pro His Thr Val Leu Asn Leu Lys
            115                 120                 125

Glu Pro Leu Tyr Val Gly Gly Ala Pro Asp Phe Ser Lys Leu Ala Arg
            130                 135                 140

Ala Ala Ala Val Ser Ser Gly Phe Asp Gly Ala Ile Gln Leu Val Ser
145                 150                 155                 160

Leu Gly Gly Arg Gln Leu Leu Thr Pro Glu His Val Leu Arg Gln Val
            165                 170                 175

Asp Val Thr Ser Phe Ala Gly His
            180

<210> SEQ ID NO 2
<211> LENGTH: 188
<212> TYPE: PRT
<213> ORGANISM: homo sapiens

<400> SEQUENCE: 2

Thr Leu Ala Phe Asp Gly Arg Thr Phe Val Glu Tyr Leu Asn Ala Val
1               5                   10                  15

Thr Glu Ser Glu Leu Ala Asn Glu Ile Pro Val Glu Lys Ala Leu Gln
            20                  25                  30

Ser Asn His Phe Glu Leu Ser Leu Arg Thr Glu Ala Thr Gln Gly Leu
        35                  40                  45

Val Leu Trp Ser Gly Lys Ala Thr Glu Arg Ala Asp Tyr Val Ala Leu
    50                  55                  60

Ala Ile Val Asp Gly His Leu Gln Leu Ser Tyr Asn Leu Gly Ser Gln
65                  70                  75                  80

Pro Val Val Leu Arg Ser Thr Val Pro Val Asn Thr Asn Arg Trp Leu
            85                  90                  95

Arg Val Val Ala His Arg Glu Gln Arg Glu Gly Ser Leu Gln Val Gly
            100                 105                 110

Asn Glu Ala Pro Val Thr Gly Ser Ser Pro Leu Gly Ala Thr Gln Leu
            115                 120                 125

```
Asp Thr Asp Gly Ala Leu Trp Leu Gly Gly Leu Pro Glu Leu Pro Val
            130                 135                 140

Gly Pro Ala Leu Pro Lys Ala Tyr Gly Thr Gly Phe Val Gly Cys Leu
145                 150                 155                 160

Arg Asp Val Val Val Gly Arg His Pro Leu His Leu Leu Glu Asp Ala
                165                 170                 175

Val Thr Lys Pro Glu Leu Arg Pro Cys Pro Thr Pro
            180                 185

<210> SEQ ID NO 3
<211> LENGTH: 421
<212> TYPE: PRT
<213> ORGANISM: Artificial
<220> FEATURE:
<223> OTHER INFORMATION: Neurotrypsin resistant agrin fragment C44 y4z8

<400> SEQUENCE: 3

Leu Ala Asp Phe Asn Gly Phe Ser His Leu Glu Leu Arg Gly Leu His
1               5                   10                  15

Thr Phe Ala Arg Asp Leu Gly Glu Lys Met Ala Leu Glu Val Val Phe
            20                  25                  30

Leu Ala Arg Gly Pro Ser Gly Leu Leu Leu Tyr Asn Gly Gln Lys Thr
        35                  40                  45

Asp Gly Lys Gly Asp Phe Val Ser Leu Ala Leu Arg Asp Arg Arg Leu
50                  55                  60

Glu Phe Arg Tyr Asp Leu Gly Lys Gly Ala Ala Val Ile Arg Ser Arg
65                  70                  75                  80

Glu Pro Val Thr Leu Gly Ala Trp Thr Arg Val Ser Leu Glu Arg Asn
            85                  90                  95

Gly Arg Lys Gly Ala Leu Arg Val Gly Asp Gly Pro Arg Val Leu Gly
        100                 105                 110

Glu Ser Pro Lys Ser Arg Lys Val Pro His Thr Val Leu Asn Leu Lys
    115                 120                 125

Glu Pro Leu Tyr Val Gly Gly Ala Pro Asp Phe Ser Lys Leu Ala Arg
130                 135                 140

Ala Ala Ala Val Ser Ser Gly Phe Asp Gly Ala Ile Gln Leu Val Ser
145                 150                 155                 160

Leu Gly Gly Arg Gln Leu Leu Thr Pro Glu His Val Leu Arg Gln Val
            165                 170                 175

Asp Val Thr Ser Phe Ala Gly His Pro Cys Thr Arg Ala Ser Gly His
        180                 185                 190

Pro Cys Leu Asn Gly Ala Ser Cys Val Pro Arg Glu Ala Ala Tyr Val
    195                 200                 205

Cys Leu Cys Pro Gly Gly Phe Ser Gly Pro His Cys Glu Lys Gly Leu
210                 215                 220

Val Glu Ala Ser Ala Gly Asp Val Asp Thr Leu Ala Phe Asp Gly Arg
225                 230                 235                 240

Thr Phe Val Glu Tyr Leu Asn Ala Val Thr Glu Ser Glu Leu Ala Asn
            245                 250                 255

Glu Ile Pro Val Glu Lys Ala Leu Gln Ser Asn His Phe Glu Leu Ser
        260                 265                 270

Leu Arg Thr Glu Ala Thr Gln Gly Leu Val Leu Trp Ser Gly Lys Ala
    275                 280                 285

Thr Glu Arg Ala Asp Tyr Val Ala Leu Ala Ile Val Asp Gly His Leu
290                 295                 300
```

```
Gln Leu Ser Tyr Asn Leu Gly Ser Gln Pro Val Val Leu Arg Ser Thr
305                 310                 315                 320

Val Pro Val Asn Thr Asn Arg Trp Leu Arg Val Val Ala His Arg Glu
                325                 330                 335

Gln Arg Glu Gly Ser Leu Gln Val Gly Asn Glu Ala Pro Val Thr Gly
            340                 345                 350

Ser Ser Pro Leu Gly Ala Thr Gln Leu Asp Thr Asp Gly Ala Leu Trp
        355                 360                 365

Leu Gly Gly Leu Pro Glu Leu Pro Val Gly Pro Ala Leu Pro Lys Ala
    370                 375                 380

Tyr Gly Thr Gly Phe Val Gly Cys Leu Arg Asp Val Val Gly Arg
385                 390                 395                 400

His Pro Leu His Leu Leu Glu Asp Ala Val Thr Lys Pro Glu Leu Arg
                405                 410                 415

Pro Cys Pro Thr Pro
                420

<210> SEQ ID NO 4
<211> LENGTH: 441
<212> TYPE: PRT
<213> ORGANISM: Artificial
<220> FEATURE:
<223> OTHER INFORMATION: Neurotrypsin resistant agrin fragment C44K/A

<400> SEQUENCE: 4

Ala Arg Val Asn His His His His His His Leu Glu Val Leu
1               5                   10                  15

Phe Gln Gly Pro Leu Ala Asp Phe Asn Gly Phe Ser His Leu Glu Leu
                20                  25                  30

Arg Gly Leu His Thr Phe Ala Arg Asp Leu Gly Glu Lys Met Ala Leu
            35                  40                  45

Glu Val Val Phe Leu Ala Arg Gly Pro Ser Gly Leu Leu Leu Tyr Asn
        50                  55                  60

Gly Gln Lys Thr Asp Gly Lys Gly Asp Phe Val Ser Leu Ala Leu Arg
65                  70                  75                  80

Asp Arg Arg Leu Glu Phe Arg Tyr Asp Leu Gly Lys Gly Ala Ala Val
                85                  90                  95

Ile Arg Ser Arg Glu Pro Val Thr Leu Gly Ala Trp Thr Arg Val Ser
                100                 105                 110

Leu Glu Arg Asn Gly Arg Lys Gly Ala Leu Arg Val Gly Asp Gly Pro
            115                 120                 125

Arg Val Leu Gly Glu Ser Pro Lys Ser Arg Lys Val Pro His Thr Val
        130                 135                 140

Leu Asn Leu Lys Glu Pro Leu Tyr Val Gly Gly Ala Pro Asp Phe Ser
145                 150                 155                 160

Lys Leu Ala Arg Ala Ala Ala Val Ser Ser Gly Phe Asp Gly Ala Ile
                165                 170                 175

Gln Leu Val Ser Leu Gly Gly Arg Gln Leu Leu Thr Pro Glu His Val
            180                 185                 190

Leu Arg Gln Val Asp Val Thr Ser Phe Ala Gly His Pro Cys Thr Arg
        195                 200                 205

Ala Ser Gly His Pro Cys Leu Asn Gly Ala Ser Cys Val Pro Arg Glu
    210                 215                 220

Ala Ala Tyr Val Cys Leu Cys Pro Gly Gly Phe Ser Gly Pro His Cys
225                 230                 235                 240
```

```
Glu Lys Gly Leu Val Glu Ala Ser Ala Gly Asp Val Asp Thr Leu Ala
            245                 250                 255

Phe Asp Gly Arg Thr Phe Val Glu Tyr Leu Asn Ala Val Thr Glu Ser
            260                 265                 270

Glu Leu Ala Asn Glu Ile Pro Val Glu Lys Ala Leu Gln Ser Asn His
            275                 280                 285

Phe Glu Leu Ser Leu Arg Thr Glu Ala Thr Gln Gly Leu Val Leu Trp
            290                 295                 300

Ser Gly Lys Ala Thr Glu Arg Ala Asp Tyr Val Ala Leu Ala Ile Val
305                 310                 315                 320

Asp Gly His Leu Gln Leu Ser Tyr Asn Leu Gly Ser Gln Pro Val Val
                325                 330                 335

Leu Arg Ser Thr Val Pro Val Asn Thr Asn Arg Trp Leu Arg Val Val
                340                 345                 350

Ala His Arg Glu Gln Arg Glu Gly Ser Leu Gln Val Gly Asn Glu Ala
            355                 360                 365

Pro Val Thr Gly Ser Ser Pro Leu Gly Ala Thr Gln Leu Asp Thr Asp
            370                 375                 380

Gly Ala Leu Trp Leu Gly Gly Leu Pro Glu Leu Pro Val Gly Pro Ala
385                 390                 395                 400

Leu Pro Lys Ala Tyr Gly Thr Gly Phe Val Gly Cys Leu Arg Asp Val
                405                 410                 415

Val Val Gly Arg His Pro Leu His Leu Leu Glu Asp Ala Val Thr Lys
                420                 425                 430

Pro Glu Leu Arg Pro Cys Pro Thr Pro
            435                 440

<210> SEQ ID NO 5
<211> LENGTH: 4
<212> TYPE: PRT
<213> ORGANISM: Artificial
<220> FEATURE:
<223> OTHER INFORMATION: Insert at the y-site of agrin (y4)

<400> SEQUENCE: 5

Lys Ser Arg Lys
1

<210> SEQ ID NO 6
<211> LENGTH: 17
<212> TYPE: PRT
<213> ORGANISM: Artificial
<220> FEATURE:
<223> OTHER INFORMATION: Insert at the y-site of agrin (y17)

<400> SEQUENCE: 6

Val Leu Ser Ala Ser His Pro Leu Thr Val Ser Gly Ala Ser Thr Pro
1               5                   10                  15

Arg

<210> SEQ ID NO 7
<211> LENGTH: 21
<212> TYPE: PRT
<213> ORGANISM: Artificial
<220> FEATURE:
<223> OTHER INFORMATION: Insert at the y-site of agrin (y21)
```

-continued

```
<400> SEQUENCE: 7

Lys Ser Arg Lys Val Leu Ser Ala Ser His Pro Leu Thr Val Ser Gly
1               5                   10                  15

Ala Ser Thr Pro Arg
            20

<210> SEQ ID NO 8
<211> LENGTH: 8
<212> TYPE: PRT
<213> ORGANISM: Artificial
<220> FEATURE:
<223> OTHER INFORMATION: Insert at the z-site of agrin (z8)

<400> SEQUENCE: 8

Glu Leu Ala Asn Glu Ile Pro Val
1               5

<210> SEQ ID NO 9
<211> LENGTH: 11
<212> TYPE: PRT
<213> ORGANISM: Artificial
<220> FEATURE:
<223> OTHER INFORMATION: Insert at the z-site of agrin (z11)

<400> SEQUENCE: 9

Pro Glu Thr Leu Asp Ser Gly Ala Leu His Ser
1               5                   10

<210> SEQ ID NO 10
<211> LENGTH: 19
<212> TYPE: PRT
<213> ORGANISM: Artificial
<220> FEATURE:
<223> OTHER INFORMATION: Insert at the z-site of agrin (z19)

<400> SEQUENCE: 10

Glu Leu Ala Asn Glu Ile Pro Val Pro Glu Thr Leu Asp Ser Gly Ala
1               5                   10                  15

Leu His Ser

<210> SEQ ID NO 11
<211> LENGTH: 417
<212> TYPE: PRT
<213> ORGANISM: Artificial
<220> FEATURE:
<223> OTHER INFORMATION: Neurotrypsin resistant agrin fragment C44 y0z8
      (h)

<400> SEQUENCE: 11

Leu Ala Asp Phe Asn Gly Phe Ser His Leu Glu Leu Arg Gly Leu His
1               5                   10                  15

Thr Phe Ala Arg Asp Leu Gly Glu Lys Met Ala Leu Glu Val Val Phe
            20                  25                  30

Leu Ala Arg Gly Pro Ser Gly Leu Leu Leu Tyr Asn Gly Gln Lys Thr
        35                  40                  45

Asp Gly Lys Gly Asp Phe Val Ser Leu Ala Leu Arg Asp Arg Arg Leu
    50                  55                  60

Glu Phe Arg Tyr Asp Leu Gly Lys Gly Ala Ala Val Ile Arg Ser Arg
65                  70                  75                  80

Glu Pro Val Thr Leu Gly Ala Trp Thr Arg Val Ser Leu Glu Arg Asn
                85                  90                  95

Gly Arg Lys Gly Ala Leu Arg Val Gly Asp Gly Pro Arg Val Leu Gly
            100                 105                 110
```

```
Glu Ser Pro Val Pro His Thr Val Leu Asn Leu Lys Glu Pro Leu Tyr
            115                 120                 125

Val Gly Gly Ala Pro Asp Phe Ser Lys Leu Ala Arg Ala Ala Ala Val
130                 135                 140

Ser Ser Gly Phe Asp Gly Ala Ile Gln Leu Val Ser Leu Gly Gly Arg
145                 150                 155                 160

Gln Leu Leu Thr Pro Glu His Val Leu Arg Gln Val Asp Val Thr Ser
                165                 170                 175

Phe Ala Gly His Pro Cys Thr Arg Ala Ser Gly His Pro Cys Leu Asn
                180                 185                 190

Gly Ala Ser Cys Val Pro Arg Glu Ala Ala Tyr Val Cys Leu Cys Pro
            195                 200                 205

Gly Gly Phe Ser Gly Pro His Cys Glu Lys Gly Leu Val Glu Ala Ser
210                 215                 220

Ala Gly Asp Val Asp Thr Leu Ala Phe Asp Gly Arg Thr Phe Val Glu
225                 230                 235                 240

Tyr Leu Asn Ala Val Thr Glu Ser Glu Leu Ala Asn Glu Ile Pro Val
                245                 250                 255

Glu Lys Ala Leu Gln Ser Asn His Phe Glu Leu Ser Leu Arg Thr Glu
            260                 265                 270

Ala Thr Gln Gly Leu Val Leu Trp Ser Gly Lys Ala Thr Glu Arg Ala
            275                 280                 285

Asp Tyr Val Ala Leu Ala Ile Val Asp Gly His Leu Gln Leu Ser Tyr
            290                 295                 300

Asn Leu Gly Ser Gln Pro Val Val Leu Arg Ser Thr Val Pro Val Asn
305                 310                 315                 320

Thr Asn Arg Trp Leu Arg Val Val Ala His Arg Glu Gln Arg Glu Gly
                325                 330                 335

Ser Leu Gln Val Gly Asn Glu Ala Pro Val Thr Gly Ser Ser Pro Leu
            340                 345                 350

Gly Ala Thr Gln Leu Asp Thr Asp Gly Ala Leu Trp Leu Gly Gly Leu
            355                 360                 365

Pro Glu Leu Pro Val Gly Pro Ala Leu Pro Lys Ala Tyr Gly Thr Gly
370                 375                 380

Phe Val Gly Cys Leu Arg Asp Val Val Val Gly Arg His Pro Leu His
385                 390                 395                 400

Leu Leu Glu Asp Ala Val Thr Lys Pro Glu Leu Arg Pro Cys Pro Thr
                405                 410                 415

Pro

<210> SEQ ID NO 12
<211> LENGTH: 417
<212> TYPE: PRT
<213> ORGANISM: Artificial
<220> FEATURE:
<223> OTHER INFORMATION: Neurotrypsin resistant agrin fragment C44 y0z8
      (m)

<400> SEQUENCE: 12

Leu Ala Asp Phe Asn Gly Phe Ser Tyr Leu Glu Leu Lys Gly Leu His
1               5                   10                  15

Thr Phe Glu Arg Asp Leu Gly Glu Lys Met Ala Leu Glu Met Val Phe
                20                  25                  30

Leu Ala Arg Gly Pro Ser Gly Leu Leu Leu Tyr Asn Gly Gln Lys Thr
            35                  40                  45
```

Asp Gly Lys Gly Asp Phe Val Ser Leu Ala Leu His Asn Arg His Leu
 50                  55                  60

Glu Phe Arg Tyr Asp Leu Gly Lys Gly Ala Ala Ile Ile Arg Ser Lys
 65                  70                  75                  80

Glu Pro Ile Ala Leu Gly Thr Trp Val Arg Val Phe Leu Glu Arg Asn
                 85                  90                  95

Gly Arg Lys Gly Ala Leu Gln Val Gly Asp Gly Pro Arg Val Leu Gly
                100                 105                 110

Glu Ser Pro Val Pro His Thr Met Leu Asn Leu Lys Glu Pro Leu Tyr
            115                 120                 125

Val Gly Gly Ala Pro Asp Phe Ser Lys Leu Ala Arg Gly Ala Ala Val
            130                 135                 140

Ala Ser Gly Phe Asp Gly Ala Ile Gln Leu Val Ser Leu Arg Gly His
145                 150                 155                 160

Gln Leu Leu Thr Gln Glu His Val Leu Arg Ala Val Asp Val Ala Pro
                165                 170                 175

Phe Ala Gly His Pro Cys Thr Gln Ala Val Asp Asn Pro Cys Leu Asn
                180                 185                 190

Gly Gly Ser Cys Ile Pro Arg Glu Ala Thr Tyr Glu Cys Leu Cys Pro
            195                 200                 205

Gly Gly Phe Ser Gly Leu His Cys Glu Lys Gly Ile Val Glu Ala Ser
            210                 215                 220

Val Gly Asp Leu Glu Thr Leu Ala Phe Asp Gly Arg Thr Tyr Ile Glu
225                 230                 235                 240

Tyr Leu Asn Ala Val Thr Glu Ser Glu Leu Thr Asn Glu Ile Pro Ala
                245                 250                 255

Glu Lys Ala Leu Gln Ser Asn His Phe Glu Leu Ser Leu Arg Thr Glu
            260                 265                 270

Ala Thr Gln Gly Leu Val Leu Trp Ile Gly Lys Val Gly Glu Arg Ala
            275                 280                 285

Asp Tyr Met Ala Leu Ala Ile Val Asp Gly His Leu Gln Leu Ser Tyr
            290                 295                 300

Asp Leu Gly Ser Gln Pro Val Val Leu Arg Ser Thr Val Lys Val Asn
305                 310                 315                 320

Thr Asn Arg Trp Leu Arg Val Arg Ala His Arg Glu His Arg Glu Gly
                325                 330                 335

Ser Leu Gln Val Gly Asn Glu Ala Pro Val Thr Gly Ser Ser Pro Leu
            340                 345                 350

Gly Ala Thr Gln Leu Asp Thr Asp Gly Ala Leu Trp Leu Gly Gly Leu
            355                 360                 365

Gln Lys Leu Pro Val Gly Gln Ala Leu Pro Lys Ala Tyr Gly Thr Gly
            370                 375                 380

Phe Val Gly Cys Leu Arg Asp Val Val Val Gly His Arg Gln Leu His
385                 390                 395                 400

Leu Leu Glu Asp Ala Val Thr Lys Pro Glu Leu Arg Pro Cys Pro Thr
                405                 410                 415

Leu

<210> SEQ ID NO 13
<211> LENGTH: 413
<212> TYPE: PRT
<213> ORGANISM: Artificial
<220> FEATURE:
<223> OTHER INFORMATION: Neurotrypsin resistant agrin fragment C44 y4z0

<400> SEQUENCE: 13

```
Leu Ala Asp Phe Asn Gly Phe Ser His Leu Glu Leu Arg Gly Leu His
  1               5                  10                  15

Thr Phe Ala Arg Asp Leu Gly Glu Lys Met Ala Leu Glu Val Val Phe
             20                  25                  30

Leu Ala Arg Gly Pro Ser Gly Leu Leu Tyr Asn Gly Gln Lys Thr
         35                  40                  45

Asp Gly Lys Gly Asp Phe Val Ser Leu Ala Leu Arg Asp Arg Arg Leu
 50                  55                  60

Glu Phe Arg Tyr Asp Leu Gly Lys Gly Ala Ala Val Ile Arg Ser Arg
 65                  70                  75                  80

Glu Pro Val Thr Leu Gly Ala Trp Thr Arg Val Ser Leu Glu Arg Asn
                 85                  90                  95

Gly Arg Lys Gly Ala Leu Arg Val Gly Asp Gly Pro Arg Val Leu Gly
            100                 105                 110

Glu Ser Pro Lys Ser Arg Lys Val Pro His Thr Val Leu Asn Leu Lys
            115                 120                 125

Glu Pro Leu Tyr Val Gly Gly Ala Pro Asp Phe Ser Lys Leu Ala Arg
            130                 135                 140

Ala Ala Ala Val Ser Ser Gly Phe Asp Gly Ala Ile Gln Leu Val Ser
145                 150                 155                 160

Leu Gly Gly Arg Gln Leu Leu Thr Pro Glu His Val Leu Arg Gln Val
                165                 170                 175

Asp Val Thr Ser Phe Ala Gly His Pro Cys Thr Arg Ala Ser Gly His
            180                 185                 190

Pro Cys Leu Asn Gly Ala Ser Cys Val Pro Arg Glu Ala Ala Tyr Val
            195                 200                 205

Cys Leu Cys Pro Gly Gly Phe Ser Gly Pro His Cys Glu Lys Gly Leu
            210                 215                 220

Val Glu Ala Ser Ala Gly Asp Val Asp Thr Leu Ala Phe Asp Gly Arg
225                 230                 235                 240

Thr Phe Val Glu Tyr Leu Asn Ala Val Thr Glu Ser Glu Lys Ala Leu
                245                 250                 255

Gln Ser Asn His Phe Glu Leu Ser Leu Arg Thr Glu Ala Thr Gln Gly
            260                 265                 270

Leu Val Leu Trp Ser Gly Lys Ala Thr Glu Arg Ala Asp Tyr Val Ala
            275                 280                 285

Leu Ala Ile Val Asp Gly His Leu Gln Leu Ser Tyr Asn Leu Gly Ser
            290                 295                 300

Gln Pro Val Val Leu Arg Ser Thr Val Pro Val Asn Thr Asn Arg Trp
305                 310                 315                 320

Leu Arg Val Val Ala His Arg Glu Gln Arg Glu Gly Ser Leu Gln Val
                325                 330                 335

Gly Asn Glu Ala Pro Val Thr Gly Ser Ser Pro Leu Gly Ala Thr Gln
            340                 345                 350

Leu Asp Thr Asp Gly Ala Leu Trp Leu Gly Gly Leu Pro Glu Leu Pro
            355                 360                 365

Val Gly Pro Ala Leu Pro Lys Ala Tyr Gly Thr Gly Phe Val Gly Cys
            370                 375                 380

Leu Arg Asp Val Val Val Gly Arg His Pro Leu His Leu Leu Glu Asp
385                 390                 395                 400

Ala Val Thr Lys Pro Glu Leu Arg Pro Cys Pro Thr Pro
                405                 410
```

```
<210> SEQ ID NO 14
<211> LENGTH: 421
<212> TYPE: PRT
<213> ORGANISM: Artificial
<220> FEATURE:
<223> OTHER INFORMATION: Neurotrypsin resistant agrin fragment C44 y4z8
      (m)

<400> SEQUENCE: 14
```

| |

```
Leu Gly Gly Leu Gln Lys Leu Pro Val Gly Gln Ala Leu Pro Lys Ala
            370                 375                 380

Tyr Gly Thr Gly Phe Val Gly Cys Leu Arg Asp Val Val Val Gly His
385                 390                 395                 400

Arg Gln Leu His Leu Leu Glu Asp Ala Val Thr Lys Pro Glu Leu Arg
                405                 410                 415

Pro Cys Pro Thr Leu
            420

<210> SEQ ID NO 15
<211> LENGTH: 427
<212> TYPE: PRT
<213> ORGANISM: Artificial
<220> FEATURE:
<223> OTHER INFORMATION: Neurotrypsin resistant agrin fragment C44 y Ile Val Asp Gly His Leu Gln Leu Ser Tyr Asn Leu Gly Ser Gln Pro
305                 310                 315                 320

Val Val Leu Arg Ser Thr Val Pro Val Asn Thr Arg Trp Leu Arg
                325                 330                 335

Val Val Ala His Arg Glu Gln Arg Glu Gly Ser Leu Gln Val Gly Asn
            340                 345                 350

Glu Ala Pro Val Thr Gly Ser Ser Pro Leu Gly Ala Thr Gln Leu Asp
            355                 360                 365

Thr Asp Gly Ala Leu Trp Leu Gly Leu Pro Glu Leu Pro Val Gly
370                 375                 380

Pro Ala Leu Pro Lys Ala Tyr Gly Thr Gly Phe Val Gly Cys Leu Arg
385                 390                 395                 400

Asp Val Val Gly Arg His Pro Leu His Leu Leu Glu Asp Ala Val
                405                 410                 415

Thr Lys Pro Glu Leu Arg Pro Cys Pro Thr Pro
            420                 425

<210> SEQ ID NO 16
<211> LENGTH: 428
<212> TYPE: PRT
<213> ORGANISM: Artificial
<220> FEATURE:
<223> OTHER INFORMATION: Neurotrypsin resistant agrin fragment C44 y0z19
      (m)

<400> SEQUENCE: 16

Leu Ala Asp Phe Asn Gly Phe Ser Tyr Leu Glu Leu Lys Gly Leu His
1               5                   10                  15

Thr Phe Glu Arg Asp Leu Gly Glu Lys Met Ala Leu Glu Met Val

-continued

```
Tyr Leu Asn Ala Val Thr Glu Ser Glu Leu Thr Asn Glu Ile Pro Ala
                245                 250                 255

Pro Glu Thr Leu Asp Ser Arg Ala Leu Phe Ser Glu Lys Ala Leu Gln
            260                 265                 270

Ser Asn His Phe Glu Leu Ser Leu Arg Thr Glu Ala Thr Gln Gly Leu
        275                 280                 285

Val Leu Trp Ile Gly Lys Val Gly Glu Arg Ala Asp Tyr Met Ala Leu
    290                 295                 300

Ala Ile Val Asp Gly His Leu Gln Leu Ser Tyr Asp Leu Gly Ser Gln
305                 310                 315                 320

Pro Val Val Leu Arg Ser Thr Val Lys Val Asn Thr Asn Arg Trp Leu
            325                 330                 335

Arg Val Arg Ala His Arg Glu His Arg Glu Gly Ser Leu Gln Val Gly
            340                 345                 350

Asn Glu Ala Pro Val Thr Gly Ser Ser Pro Leu Gly Ala Thr Gln Leu
        355                 360                 365

Asp Thr Asp Gly Ala Leu Trp Leu Gly Gly Leu Gln Lys Leu Pro Val
    370                 375                 380

Gly Gln Ala Leu Pro Lys Ala Tyr Gly Thr Gly Phe Val Gly Cys Leu
385                 390                 395                 400

Arg Asp Val Val Val Gly His Arg Gln Leu His Leu Leu Glu Asp Ala
            405                 410                 415

Val Thr Lys Pro Glu Leu Arg Pro Cys Pro Thr Leu
            420                 425
```